US012766263B2

(12) United States Patent
Arocha

(10) Patent No.: US 12,766,263 B2
(45) Date of Patent: Oct. 20, 2026

(54) PARTITIONED CARPULE, SYRINGE, AND SYSTEM THEREFOR, AND METHODS OF USE THEREOF

(71) Applicant: PHARMAPHDII, LLC, Plantation, FL (US)

(72) Inventor: Max Arocha, Plantation, FL (US)

(73) Assignee: PHARMAPHDII, LLC, Plantation, FL (US)

( * ) Notice: Subject to any disclaimer, the term of this patent is extended or adjusted under 35 U.S.C. 154(b) by 602 days.

(21) Appl. No.: 18/010,187

(22) PCT Filed: Jun. 14, 2021

(86) PCT No.: PCT/US2021/037228
§ 371 (c)(1),
(2) Date: Dec. 13, 2022

(87) PCT Pub. No.: WO2021/253000
PCT Pub. Date: Dec. 16, 2021

(65) Prior Publication Data

US 2023/0248915 A1 Aug. 10, 2023

Related U.S. Application Data

(60) Provisional application No. 63/038,765, filed on Jun. 13, 2020.

(51) Int. Cl.
*A61M 5/24* (2006.01)
*A61M 5/315* (2006.01)

(52) U.S. Cl.
CPC ...... *A61M 5/2448* (2013.01); *A61M 5/31578* (2013.01); *A61M 2005/2414* (2013.01)

(58) Field of Classification Search
CPC ......... A61M 5/19; A61M 5/2448; A61M 5/24
See application file for complete search history.

(56) References Cited

U.S. PATENT DOCUMENTS 4,631,055 A * 12/1986 Redl ................ A61B 17/00491 604/82
4,689,042 A * 8/1987 Sarnoff ............... A61M 5/2066 604/191
4,874,368 A * 10/1989 Miller .............. A61B 17/00491 604/82
5,147,323 A * 9/1992 Haber ................... A61M 5/322 604/232
5,240,146 A * 8/1993 Smedley ............... A61M 5/315 604/82
5,290,259 A * 3/1994 Fischer ................... A61M 5/19 222/137
5,314,412 A * 5/1994 Rex ..................... A61M 5/2448 604/82

(Continued)

FOREIGN PATENT DOCUMENTS

AT 382783 B * 4/1987 .............. A61M 5/19

*Primary Examiner* — Adam Marcetich
*Assistant Examiner* — Ted Yang
(74) *Attorney, Agent, or Firm* — Ted Whitlock; Ted Whitlock Registered Patent Attorney, PA

(57) ABSTRACT

Described is a mixing syringe for receiving a removable carpule partitioned to form two reservoirs independently containing anesthetic solution and buffering solution and having a mixing chamber for mixing the solutions during administration, and methods of using the mixing syringe.

9 Claims, 4 Drawing Sheets

(56) References Cited

U.S. PATENT DOCUMENTS

| | | | | |
|---|---|---|---|---|
| 5,505,704 | A * | 4/1996 | Pawelka | A61M 5/31581 604/82 |
| 5,542,934 | A * | 8/1996 | Silver | A61M 5/19 604/232 |
| 5,584,815 | A * | 12/1996 | Pawelka | A61M 5/19 604/83 |
| 5,685,846 | A * | 11/1997 | Michaels, Jr. | A61M 5/31596 604/82 |
| 6,547,101 | B1 * | 4/2003 | Sogaro | A61M 5/19 222/137 |
| 10,420,888 | B2 * | 9/2019 | Arocha | A61M 5/19 |
| 2008/0144433 | A1 * | 6/2008 | Renfro | B01F 25/45 222/130 |
| 2010/0318063 | A1 * | 12/2010 | Soll | A61M 5/19 604/82 |
| 2011/0245866 | A1 * | 10/2011 | Cassingham | A61B 17/00491 606/213 |
| 2013/0131632 | A1 * | 5/2013 | Mudd | A61M 5/1407 604/506 |
| 2014/0031763 | A1 * | 1/2014 | Soma | A61M 5/345 604/208 |
| 2014/0350460 | A1 * | 11/2014 | Moore | A61M 5/19 604/89 |
| 2015/0065993 | A1 * | 3/2015 | Arocha | A61M 5/19 604/87 |
| 2015/0141928 | A1 * | 5/2015 | Laugere | A61M 5/2448 29/525 |
| 2017/0281870 | A1 * | 10/2017 | Kai | B05B 7/2472 |
| 2017/0327296 | A1 * | 11/2017 | Ettlin | B01F 35/522 |
| 2018/0344574 | A1 * | 12/2018 | Oelz | A61J 7/0053 |
| 2019/0022316 | A1 * | 1/2019 | Bendix | A61M 5/326 |
| 2019/0262539 | A1 * | 8/2019 | Csenar | A61M 5/2448 |
| 2019/0321021 | A1 * | 10/2019 | Guo | A61M 5/2422 |
| 2020/0171243 | A1 * | 6/2020 | Villain | A61M 5/19 |
| 2020/0238009 | A1 * | 7/2020 | Koh | A61L 24/104 |
| 2021/0369974 | A1 * | 12/2021 | Villadsen | A61M 5/2448 |

* cited by examiner

PARTITIONED CARPULE, SYRINGE, AND SYSTEM THEREFOR, AND METHODS OF USE THEREOF

BACKGROUND OF THE INVENTION

Local anesthetics are the safest and most effective drugs in medicine for the prevention and management of pain.

Among the more commonly used local anesthetics is the amide local anesthetic, lidocaine, which is suitable for infiltration, block, and surface anesthesia. In dental medicine, lidocaine, or its hydrochloride salt, is used as a pre-mixed solution with epinephrine. Whether used alone or mixed with epinephrine, lidocaine and its salt solutions are generally acidic.

Buffering or alkalinization of local anesthetics has long been reported in the scientific literature as improving onset time and making the injection of a local anesthetics less painful and more comfortable to the patient. The terms "anesthetics buffering", "alkalinization" and "pH buffering" are recognized medical terms used for neutralizing the acidity of local anesthetics to physiological pH (7.4) before injection. Bicarbonate solution, such as sodium bicarbonate ($NaHCO_3$) in water, is routinely used to buffer the pH of local anesthetics. However, bicarbonates cannot be pre-mixed with lidocaine due to instability of the combination over time.

Mixing devices for pre-mixing anesthetic and buffer solutions remotely (away from the patient), and immediately prior to administration, are known and in common use. However, these conventional methods and devices for buffering or alkalinizing local anesthetics still have disadvantages:

1. Commercially available mixing devices involve a high degree of technique and require manual, on-site mixing of the bicarbonate with the anesthetic, immediately prior to filling of the syringe for administration of the buffered anesthetic;
2. On-site preparation time is greater than the actual time required to administer buffered anesthetic mixture.
3. Buffered anesthetic solution prepared in bulk results in decreased pH of the solution over time, resulting in diminished activity.
4. Freshly mixing buffered anesthetic solutions for subsequent administrations requires repeated and redundant preparation steps.

Technological advances have failed to address these problems and provide efficient means for mixing anesthetic and buffer immediately prior to or concomitantly with administration in a practical and easy-to-use manner in a clinical setting. For example, modifications and improvements have been made to conventional syringes to control the pH of the local anesthetic solution as it is administered.

Mixing syringes for mixing two fluids such as a local anesthetic and a buffering agent within the syringe barrel immediately before administration have been described. These are configured to provide separate, axially aligned chambers "stacked" one on top of the other within the syringe barrel or, alternatively, are configured such that the chambers are configured parallel to one another, or "side-by-side," within the syringe barrel. The vast majority of these devices relate to open lumen syringe barrels that cannot receive a prefabricated carpule of drug and diluent, i.e., they are not "cartridge" syringes or "carpule" syringes, as these terms are recognized and known in the art. More recently, U.S. Pat. No. 10,420,888 describes a side-by-side dual-barrel cartridge syringe for receiving two single carpules or one dual carpule. However, these prior attempts have been unable to resolve the problems in a cost-efficient manner.

What is needed is a dispensing device and method which can overcome these known disadvantages and deficiencies.

SUMMARY OF THE INVENTION

The subject invention concerns a partitioned carpule for use in a system and method for dispensing or administering a mixture of drug solution and diluent buffer solution from a single carpule of conventional size and shape placed within a "cartridge syringe." A cartridge syringe is sometimes synonymously termed a "carpule syringe." A cartridge syringe is a specialty syringe well known in the art and comprises a syringe housing, typically metal, having an opening or window capable of receiving a carpule or cartridge containing drug or diluent, or both. More specifically, the subject invention relates to a partitioned carpule for use in an aspirating cartridge syringe. An aspirating syringe comprises a harpoon at a proximal end of its plunger stem to engage with and manipulate a cap slidingly disposed in the distal end of the carpule. A stationary end cap is disposed in a proximal end of the carpule, wherein the distal and proximal end caps retain the contents of the carpule therein.

All references to a "syringe" used herein, refer to an aspiration cartridge syringe for use with a single carpule.

For purposes of the subject invention, the terms "distal" or "superior" and "proximal" and "inferior" are used to describe the relative position of the components of the syringe or system. "Distal" or "superior" refers to the end farthest away from the patient when the syringe is used, i.e., the end from which the user of the syringe actuates the plunger; "proximal" or "inferior" refers to the end closest to the patient when in use, i.e., the end of the syringe engaged with a hypodermic needle.

The terms "axial," "longitudinal," or "longitudinal axis," or "axial length" all refer to a relative position or direction along one or more long axis or length dimension of the generally cylindrical syringe and carpule of the invention.

A standard cartridge syringe used in the medical or dental fields comprises a cylindrical barrel, typically formed of a metal, wherein the barrel has an opening or window in a side wall for receiving and removing a single carpule containing drug or diluent. At its distal end, the barrel of the standard syringe can comprise a flange or flanges forming a finger-hold to facilitate actuation of a plunger for expelling the contents from the barrel or a carpule contained within the barrel.

The cartridge syringe comprises a plunger which includes a piston or stem portion which slidingly engages the barrel at the flanged end of the barrel and, at its distal end, can comprise a thumbpiece—typically a flange or ring—for placement of a user's thumb and actuation of the plunger by a pushing motion which slidingly pushes the distal end cap of the carpule toward the proximal end of the carpule to expel the contents therefrom. In an aspiration syringe, the harpoon engages the distal end cap of the carpule such that a pulling motion on the fingerhold can actuate the plunger in an opposite direction, allowing the distal end cap of the carpule to be drawn or pulled back toward its original distal position.

A standard aspiration cartridge syringe also includes a delivery port at its proximal end and comprises a hub capable of engaging a removable hypodermic transfer needle.

In one embodiment of the invention, a syringe and system according to the subject invention comprises the above features, but can differ in its plunger configuration, by the carpule used, and by inclusion of a mixing chamber. For example, the subject invention can include a syringe having a modified plunger wherein the plunger stem or piston is divided or split along part of its length, or longitudinal axis, and therefore comprises a slot from its proximal end, effectively forming dual stems, each of which engage with corresponding end caps in an axially partitioned carpule. The slot can run the entire length of the stem up to the plunger flange at its distal end or can run a portion of its length, wherein the slotted stem is adjoined at its proximal end and adjoins the plunger flange as a single, unslotted stem. The adjoined section can be from 1-25 mm in length and is determined by the length of the slot, which should be capable of traversing the length of the carpule to completely expel the contents thereof.

An axially partitioned carpule is also part of the subject invention. Preferably, an axially partitioned carpule comprises an asymmetrically disposed partition, i.e., disposed off-center from the longitudinal midline, forming two asymmetric longitudinal reservoirs within the chamber of the carpule—one reservoir having a smaller volume and the other reservoir having a larger volume relative to one another. The smaller reservoir typically contains anesthetic solution, and the larger reservoir typically contains diluent or buffer solution.

To further facilitate mixing of the contents of a partitioned carpule, a syringe of the subject invention can comprise a mixing chamber positioned between the syringe barrel and the delivery port. The mixing chamber can include a wall that separates the mixing chamber from the syringe barrel, but in such configuration will include a piercing needle for traversing the proximal end cap of a partitioned carpule to allow fluid communication between the carpule and the mixing chamber.

In an embodiment of the invention which employs a longitudinally partitioned carpule having two proximal end caps—one end cap for each chamber of the partitioned carpule, the mixing chamber includes two piercing needles, one piercing needle for traversing each proximal end cap of the carpule. In an embodiment comprising two piercing needles, the piercing needles can be formed separately, providing individual conduits to deliver solution from each of the respective reservoirs of the carpule to the mixing chamber, or the two piercing needles can adjoin into a single conduit such that the contents from each dual reservoir are delivered to the mixing chamber via the single conduit.

The mixing chamber preferably comprises a turbulence apparatus disposed therewithin and separate from the mixing chamber itself, which serves to create turbulent flow of the solutions entering the mixing chamber from the partitioned carpule reservoirs, resulting in thorough mixing of the solutions immediately prior to administration of the buffered anesthetic solution through the delivery port and hypodermic transfer needle. In one preferred embodiment, the turbulence apparatus is an inert material separate and distinct from the mixing chamber, and is not formed as an integral part of the mixing chamber, i.e., it is a distinct apparatus that is not etched or formed into the wall of the mixing chamber. A preferred turbulence apparatus can be made of plastic or metal which does not interact chemically or physically with the buffered anesthetic solution and can be provided in a highly twisted or convoluted or highly porous configuration, e.g., steel wool, to facilitate turbulent flow and mixing of the solutions.

The mixing chamber comprising the turbulence apparatus preferably provides a substantially homogeneous mixture of buffer and anesthetic solutions.

In an embodiment of the syringe of the invention used with a longitudinally partitioned carpule, the syringe comprises a slotted plunger stem, wherein a slot is provided along the length of the plunger stem, to split or divide the stem into two asymmetric plunger stem portions along at least a part of, and preferably substantially the entirety of its length. Preferably, the slot is offset from the central axial plane of the plunger stem, thereby forming a single plunger stem which is asymmetrically divided into the two plunger stem portions. Each of the divided plunger stem portions is preferably shaped as a semicircle in cross-section.

Each proximal end of the slotted plunger stem portions can comprise a harpoon which can engage, and hold corresponding distal caps on a partitioned carpule, enabling the user to draw or pull back on the plunger to aspirate the syringe, as is understood in the art to determine proper location of the needle in the injection site.

The syringe of the subject invention comprising the slotted plunger stem is configured for use with a longitudinally partitioned carpule. The partitioned carpule of the invention comprises a partition disposed along the entire length of the carpule forming a single carpule comprising dual reservoirs therewithin. Each reservoir of the partitioned carpule comprises a sliding cap at its distal end. The partitioned carpule comprises at least one stationary cap or stopper at its proximal end. The partition within the carpule forming the reservoirs is preferably positioned asymmetrically, offset from the axial center, to form two reservoirs, side-by-side, each respectively containing desired volumes of the anesthetic solution and bicarbonate solution to provide the solutions at a pre-determined and desired ratio when mixed and administered to a patient.

Therefore, in one preferred embodiment of the invention, novel features of the syringe and system of the invention include but are not limited to:

a partitioned carpule forming a single, dual-reservoir carpule, wherein the respective reservoirs separately and independently contain a drug solution and a buffering agent at a predetermined amount and desired ratio;

a mixing chamber containing therewithin a turbulence apparatus for receiving and mixing the drug solution and buffering agent expelled from the partitioned carpule; and a longitudinally slotted plunger stem which provides for separate, but simultaneous, engagement with a sliding cap provided on each reservoir of the partitioned carpule, and for simultaneously plunging each reservoir of the partitioned carpule to expel and deliver the contained anesthetic solution and buffer solution from the partitioned carpule into the mixing chamber for injection of the mixture and administration to the patient.

It is therefore one object of the present invention to provide a system comprising an aspirating cartridge syringe which is inexpensive to manufacture, reusable, capable of being sterilized, and efficient in operation.

Another object of the present invention is to provide a mixing syringe that can deliver freshly mixed anesthetic and buffer solution, without remote pre-mixing or repeated mixing steps for subsequent administrations of anesthetic and buffer.

A further object of the present invention is to provide a mixing syringe which provides adequately mixed solutions that are accurately measured and accurately proportioned in predetermined amounts and ratios, for administration from a single, partitioned carpule.

Yet another object of the present invention is to provide a mixing syringe which can reduce waste of buffered drug solution and increase efficiency by reducing the time and effort expended by a health care professional to remotely pre-mix anesthetic and buffer solutions prior to administration of the mixture to a patient.

Still another object of the invention is to provide a mixing syringe which can provide freshly mixed solutions and preventing decrease of pH of the solution over time when multiple, staggered injections are required during a lengthy medical procedure.

It is another object of the invention to provide a mixing syringe in which a single, partitioned carpule having substantially standard size and shape can be readily and easily inserted into the cartridge syringe barrel, whereby the anesthetic solution and buffer solution can be mixed together immediately before administration by actuation of a single plunger, and the mixture of anesthetic and buffer solutions administered to a patient without pre-mixing or remote mixing of the solutions.

Another object of the present invention is to provide a method of mixing buffered local anesthetic solution which can obviate the need for on-site, remote (away from the patient) mixing devices and methods for pre-mixing a buffered anesthetic solution prior to loading into a syringe for administration.

One object of the present invention is to provide a disposable dual-reservoir, partitioned carpule which may be readily and easily inserted into a cartridge syringe barrel configured for receiving and use of a conventional carpule, and which can be readily and easily removed therefrom after use, thereby requiring no additional pre-mixing steps as compared to the use of a conventional syringe.

Another object of the present invention is to provide a syringe device that can administer local anesthetics at, or near, physiological pH by controlling the pH of the solution exiting the mixing chamber from the syringe device.

These objects or advantages of the subject device and method, as well as other embodiments, objects or advantages not expressly provided, would be apparent and readily understood by the description and drawings provided herein.

Figure 1:
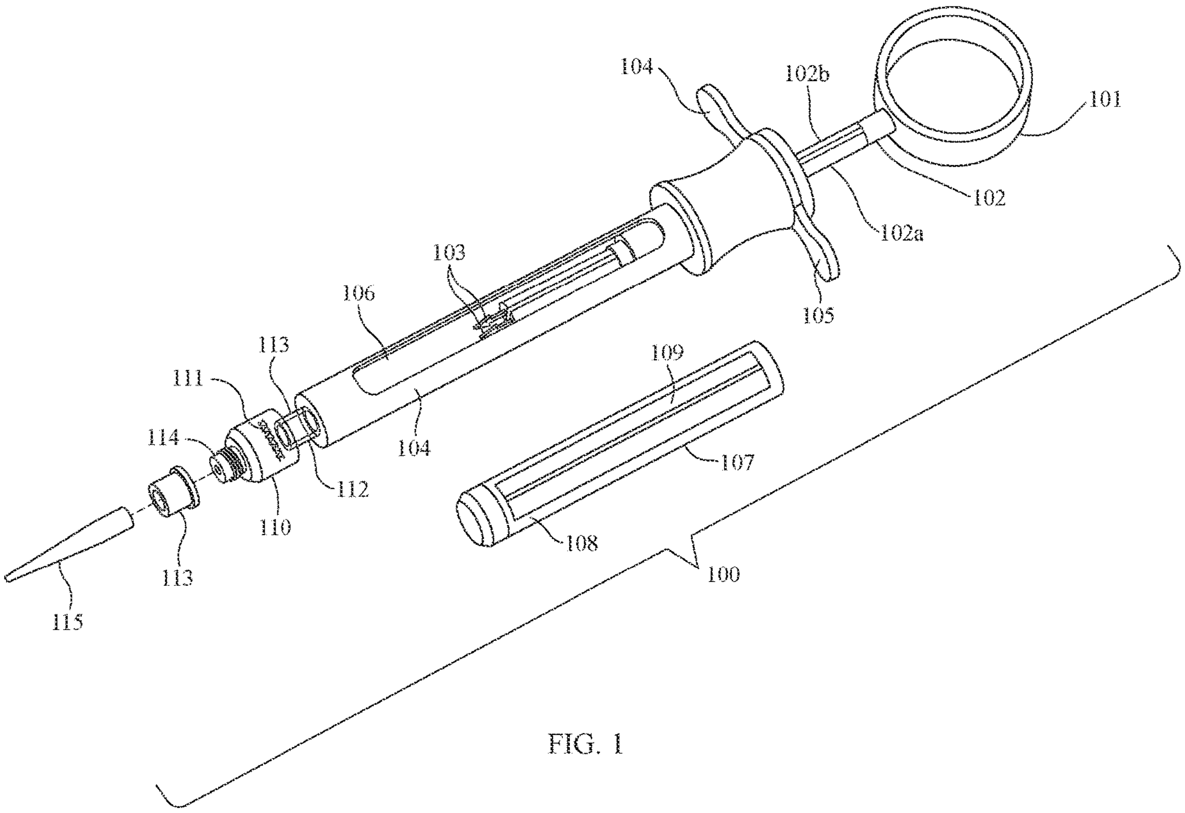
FIG. 1 is a perspective exploded view of an embodiment of a syringe device and system in accordance with the subject invention, illustrating a plunger comprising a slotted plunger stem and cross-sectional view of a partitioned carpule.

The drawings presented in this application are not to scale.

DETAILED DESCRIPTION OF THE INVENTION

The subject invention concerns a partitioned carpule and a system for mixing and delivering buffered anesthetic to a patient without requiring remote mixing of the anesthetic and buffer prior to administration. The invention includes use of the carpule in a conventional cartridge syringe, preferably a conventional aspiration cartridge syringe, or can employ a modified cartridge syringe.

The delivery system according to the subject invention comprises a carpule partitioned to provide dual, asymmetric reservoirs within the carpule, each reservoir respectively containing a drug solution and a buffering solution. The partitioned carpule can include a longitudinally divided chamber.

The invention can employ a conventional cartridge syringe or can employ a syringe modified to comprise a mixing chamber for receiving and mixing the drug solution and buffering agent expelled from the partitioned carpule and containing therewithin the mixing chamber, a turbulence apparatus. In an embodiment comprising a longitudinally partitioned carpule, a syringe of the invention can include a longitudinally slotted plunger stem forming two asymmetric plunger stem portions which separately, but simultaneously engage a sliding cap on a distal end of each carpule reservoir for plunging each reservoir of the partitioned carpule simultaneously and expelling the contents therefrom into the optional mixing chamber.

In one embodiment, the partitioned carpule of the invention comprises a partition disposed along the entire length of the carpule forming dual, asymmetric reservoirs within the single carpule, each reservoir comprising a sliding cap at its distal end and a stopper at its proximal end. Advantageously, the partition within the carpule forming the reservoirs does not divide the carpule into equal-volume reservoirs; rather, the partition is offset from the longitudinal midline, forming asymmetrical reservoirs proportionately dividing the carpule reservoirs according to the desired and predetermined amounts and ratios of anesthetic solution and buffering solution when mixed and administered.

The subject syringe device and system includes a plunger stem comprising a slot formed along its length. Although the slotted plunger stem can be divided along its entire length, effectively forming two half stems wherein each adjoin to a thumbpiece at their respective distal ends, the plunger stem preferably comprises a slot along a portion of its length, i.e., the slot does not extend the entire length of the plunger stem, and forms an intact distal segment that is adjoined and is not slotted.

In a preferred embodiment, the slot along the length of the plunger stem forms two plunger stem portions which are separate from one another at their proximal ends and adjoin at their distal ends and form a single plunger stem for that adjoined segment. Thus, in the preferred embodiment, the plunger comprises a slotted stem segment along most, between 50-99%, of its length, and has an adjoined, single-stem segment for the remaining portion of its length. Although not limited except for practical purposes, this distal unslotted segment typically can measure about 0.5 mm to about 10 mm from the distal end, where the unslotted segment adjoins or is formed integral with the thumbpiece.

More specifically, the length of the slot in the plunger stem is formed at least the distance required to fully expel the contents of the reservoirs of the partitioned carpule, with the remainder of the plunger stem being adjoined. Typically, a conventional carpule is about 5-8 cm in length. Accordingly, the length of the slot is at least about 5 cm along the length of the plunger stem and up to about 10 mm in length but less than the entire length of the plunger stem. Therefore, the length of the slot is dependent on the travel distance required to traverse the length of the carpule partition.

The slotted plunger stem portions are preferably semicircular in cross-section, corresponding to the partitioned carpule reservoirs which are also semicircular in cross-section. Thus, the slotted plunger stem portions matingly slide into the carpule reservoirs to efficiently push the reservoir caps distally, toward the distal reservoir stopper or stoppers to expel the contents of the reservoirs into the mixing chamber and then to the delivery port and transfer needle for injection and administration to the patient.

When the plunger is actuated, the slot of the plunger stem traverses the length of the partition to engage and push the sliding cap at the distal end of each carpule reservoir the entire length of the carpule until it meets the stopper disposed at the proximal end of the carpule to permit expelling a portion and up to the entire contents of the carpule chambers through a conduit comprising two piercing needles positioned proximal to the carpule and distal to the mixing chamber. The piercing needles provide for fluid communication between the carpule reservoirs and the mixing chamber.

In addition, each proximal end of the slotted plunger stem portions can include a grasping implement or harpoon protruding from their proximal ends which can engage the sliding distal end caps of the partitioned carpule to allow for pulling or drawing back of the tip in the opposite direction for aspiration (testing whether the needle has entered a blood vessel.) These harpoons are conventional in the art.

In an embodiment of a mixing syringe of the subject invention, the proximal end of each plunger stem portion comprises a harpoon whereby, depression or actuation of the plunger thumbpiece pushes the slotted plunger stem to engage the distal carpule reservoir caps. The stabs are not permanently, rather removably engaged with the partitioned carpule caps, and can be removed for disengaging the partitioned carpule from the mixing syringe barrel.

One embodiment of the invention provides a mixing syringe which comprises a mixing chamber positioned between, and in fluid communication with, the syringe barrel and the delivery port. The mixing chamber is capable of receiving the anesthetic solution and buffering solution from a single, partitioned carpule for mixing of the solutions. A wall separates the mixing chamber from the syringe barrel, but includes two piercing needles, each piercing needle traversing a stopper in the proximal end of a carpule having dual reservoirs so that, when engaged, the contents in the dual reservoirs of the carpule are in fluid communication with the mixing chamber. The piercing needles can be separate, where each piercing needle delivers solution to the mixing chamber from each of the respective reservoirs of the carpule, or can adjoin into a single conduit such that the contents from each dual reservoir are delivered to the mixing chamber via the single conduit.

The mixing chamber preferably comprises a turbulence apparatus disposed therewithin which serves to create turbulent flow of the solutions entering the mixing chamber from the partitioned carpule reservoirs, resulting in thorough mixing of the solutions immediately prior to administration of the buffered anesthetic solution through the delivery port and hypodermic transfer needle.

In one preferred embodiment, the turbulence apparatus is an inert material separate and distinct from the mixing chamber, and is not formed as an integral part of the mixing chamber, i.e., it is a distinct apparatus that is not etched or formed into the wall of the mixing chamber. A preferred turbulence apparatus can be made of plastic or metal which does not interact chemically or physically with the buffered anesthetic solution and can be provided in a twisted or convoluted or highly porous configuration, e.g., steel wool, to facilitate turbulent flow and mixing of the solutions. Alternatively, the turbulence apparatus can be a finned disc or turbine which can facilitate mixing of the solutions by a rotational motion activated by fluid passing by the apparatus. The mixing chamber comprising the turbulence apparatus preferably provides a substantially homogeneous mixture of buffer and anesthetic solutions.

The subject invention further comprises a method of administering a mixture of anesthetic solution and buffering solution, forming a mixed, buffered anesthetic solution by employing a novel syringe as described and shown herein.

Advantages of the present invention include convenience of use and greater efficiency in a clinical setting for injectable drugs, such as anesthetics, which are commonly remotely mixed with another solution immediately prior to administration. This advantage is achieved by providing a dispensing device in accordance with the subject invention comprising a syringe barrel adapted to receive a single, asymmetrically partitioned carpule having dual reservoirs for containing anesthetic solution in a first reservoir and a buffering solution in a second reservoir.

A mixing cartridge syringe and partitioned carpule of the subject invention can be a self-contained anesthetic/buffer solution mixing and delivery system which does not require pre-mixing of the anesthetic and buffer prior to loading the syringe with anesthetic or buffer solution, nor does it require mixing to be conducted remotely or outside the syringe or system of the invention.

Turning to the drawings provided herewith, FIG. 1 shows an exploded view of an embodiment of a mixing syringe and system 100 according to the subject invention. Shown is the thumbpiece 101 at a distal end of the syringe device. Affixed or integral with the thumbpiece is a plunger stem comprising a slot formed therein to provide a slotted plunger stem comprising two plunger stem portions 102*a* and 102*b*. The proximal end of each plunger stem portion comprises a stab 103. The slotted plunger stem and plunger stem portions slidingly engage the syringe barrel 103, having at its distal end at least one flange 105 forming a fingerhold. Illustrated in FIG. 1 is a mixing syringe comprising two flanges 105 to form two fingerholds.

The mixing syringe barrel 103 comprises an opening 106 or aperture in its side wall to provide for insertion and removal of a carpule containing injectable solutions. In accordance with the subject invention, a mixing syringe system includes a partitioned carpule 107, shown in cross-section in FIG. 1 to illustrate the partition asymmetrically disposed along the length of the carpule and forming dual, asymmetric reservoirs 108 and 109 therewithin.

Proximal to the mixing syringe barrel is mixing chamber 110, having a turbulence apparatus 111 disposed therein. For fluid communication between the carpule reservoirs and the mixing chamber, piercing needles 112 and 113 are provided as conduits to deliver the anesthetic and buffer solutions from the partitioned carpule into the mixing chamber. Each penetrating needle 112 and 113 can be independent from one another to deliver the solutions to the mixing chamber, or they can adjoin, proximal to the carpule reservoirs to form a single conduit for delivery of both solutions into the mixing chamber.

The mixing chamber connects proximally to a delivery port 114, which is adapted to receive and removably engage a standard hypodermic transfer needle 115, which is typically provided with a safety cap 116.

Figure 2A:
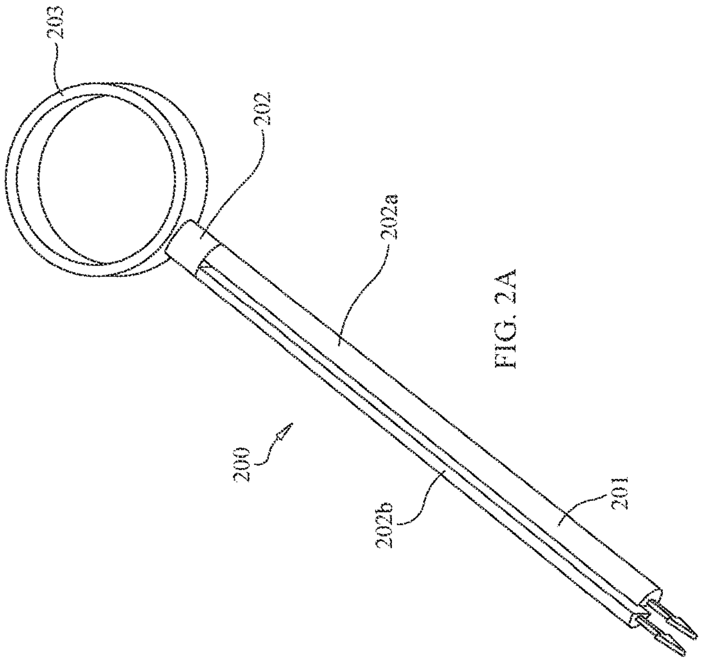
FIG. 2A is a perspective view of an embodiment of a plunger removed from the syringe body, as used in a syringe according to the subject invention, illustrating a plunger stem comprising a longitudinal slot along its length, forming two asymmetric plunger stem portions.

An embodiment of the unique slotted plunger stem 200 of the invention is further illustrated in FIG. 2. FIG. 2A shows a perspective view of the slotted plunger stem isolated from the syringe barrel. As shown, slot 201 is formed along the length of the stem, forming divided plunger stem portions 202*a* and 202*b*, which can adjoin at their distal ends to provide a single intact plunger stem section 202. The slotted plunger stem adjoins a thumbpiece 203 at the extreme distal end, and each plunger stem portion 202*a* and 202*b* has a stab 204 at its proximal end.

Figure 2B:
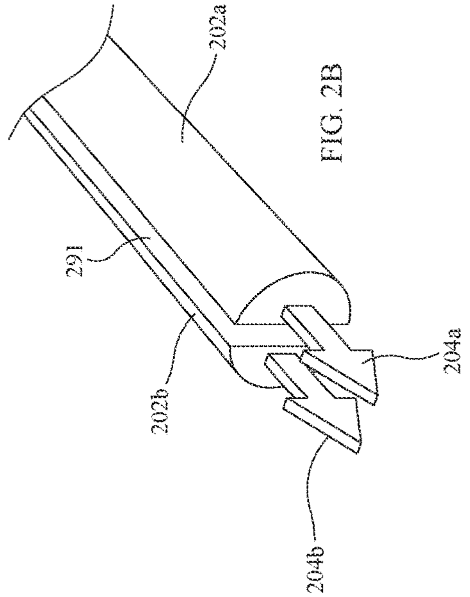
FIG. 2B is a detailed perspective view of the proximal end of the slotted plunger stem, showing the semicircular cross-sectional shape of each plunger stem portion and illustrating the presence of a grasping implement or "catch" provided on the proximal end of each plunger stem portion.

FIG. 2B is a detailed view of the proximal ends of the slotted plunger stem portions 202*a* and 202*b*. Specifically illustrated is the asymmetric configuration of plunger stem portions 202*a* and 202*b*, where slot 201 is offset from the central axial plane. FIG. 2B also illustrates the semicircular cross-sectional shape of the plunger stem portions. Stabs 204*a* and 204*b*, provided on a proximal end of each plunger stem portion are also shown, illustrated in a conventional arrowhead shape.

Figure 3A:
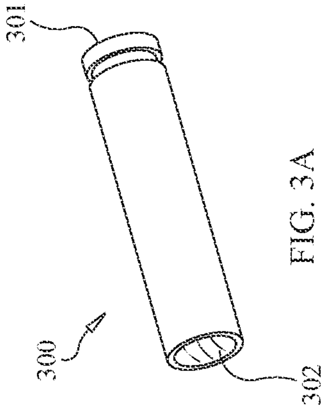
FIG. 3A is a perspective view of an embodiment of a partitioned carpule in accordance with the subject invention, illustrating its standard shape and size for use in a conventionally configured syringe barrel.
Figure 3B:
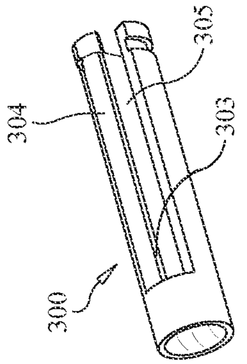
FIG. 3B is a cross-sectioned perspective view of a carpule of FIG. 3A, illustrating the partition disposed therewithin forming dual, asymmetric reservoirs within the carpule.

FIGS. 3 and 4 illustrate the configurations of a carpule used in accordance with the subject invention. FIG. 3A illustrates an outer, perspective view of a partitioned carpule 300, showing its standard shape and size for use in the mixing syringe system of the subject invention. The partitioned carpule of the invention comprises a stopper 302 at its proximal end. FIG. 3B illustrates a sectioned perspective view of a carpule 300 of the invention, showing a partition 303 asymmetrically disposed along the length of the carpule, forming asymmetric dual reservoirs 304 and 305 within the carpule. Each reservoir 304 and 305 separately and independently contains either an anesthetic solution or a buffering solution.

Figure 4A:
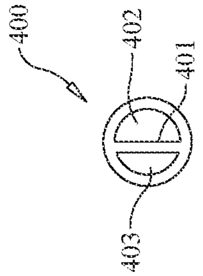
FIG. 4A is a plan view of the distal end of a partitioned carpule used in accordance with the subject invention, illustrating a partition provided along the length of the carpule to form dual, asymmetric reservoirs within the carpule.
Figure 4B:
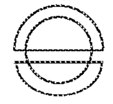
FIG. 4B is a plan view of the stoppered distal end of a partitioned carpule of FIG. 4A in accordance with the subject invention.
Figure 4C:
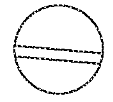
FIG. 4C is a plan view of a proximal end of a partitioned carpule according to the subject invention, illustrating the asymmetric partition disposed along the length of the carpule to form dual, asymmetric reservoirs within the carpule.
Figure 4D:
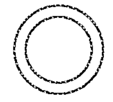
FIG. 4D shows illustrates a capped-end embodiment of the carpule of FIG. 4C.

FIG. 4A is a plan view of the distal end of a partitioned carpule 400, without sliding caps, further illustrating the asymmetric configuration, and positioning of partition 401 to form asymmetric reservoirs 402 and 403 within the carpule. FIG. 4B shows the same view as FIG. 4A, illustrating the reservoir caps positioned onto the distal end of the carpule. FIG. 4C shows a plan view of a distal end of a carpule of the invention, illustrating an embodiment comprising two stoppers respectively provided on the proximal ends of each reservoir in a partitioned carpule. FIG. 4D shows an embodiment of a partitioned carpule comprising a single stopper for both reservoirs of the carpule.

Figure 5:
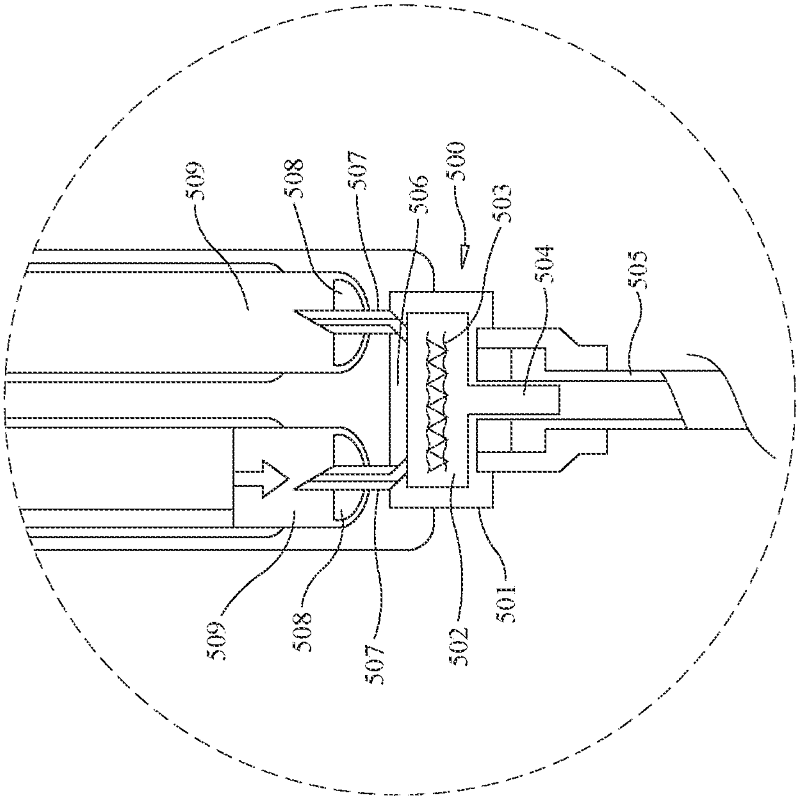
FIG. 5 is a detailed view of a mixing chamber provided with a mixing syringe according to the subject invention.

FIG. 5 illustrates a detailed plan view of a mixing chamber 500 employed with the mixing syringe of the subject invention. Mixing chamber 500 comprises a housing 501 bounding a chamber 502 into which anesthetic solution and buffer solution are received for mixing. To facilitate mixing of the solutions, the mixing chamber comprises a turbulence apparatus 503. At its proximal end, mixing chamber 500 comprises an exit port 504 through which the mixed, buffered anesthetic solution is delivered to a delivery port 505 of the syringe. The delivery port 505 of the mixing syringe is configured to receive a standard, removable hypodermic transfer needle. Wall 506 formed at a proximal end of the housing includes two piercing needles 507 which traverse carpule stoppers 508 forming conduits in fluid communication with carpule reservoirs 509.

The first and second reservoirs are provided to respectively and discretely contain an anesthetic solution and a buffer solution, each reservoir independently containing a single content of either an anesthetic solution or a buffer solution.

The present invention provides advantages over prior devices in, at least the following ways:

- it allows for mixing and dispensing local anesthetic and buffering solution from a single syringe using prefabricated carpules dispensed in a single actuating step;
- it provides a method of mixing an anesthetic solution with a buffering solution which provides a convenient and all-in-one step of producing a thorough and precise mixture of buffered anesthetic solution;
- it does not require any activation step; therefore, it is better suited for practicality and efficiency in a clinical setting.
- it provides a method of mixing buffered local anesthetic solution which will obviate the necessity of any mixing steps prior to loading into a syringe for administration;
- it provides a dual-reservoir carpule having substantially standard size and shape which may be readily and easily inserted into a conventional syringe barrel for use, and readily and easily removed therefrom after use;
- it provides a disposable readily and easily inserted carpule comprising dual reservoirs prefilled with sodium bicarbonate solution local anesthetic solution readily available for mixing or dispensing;
- it provides a syringe assembly with a mixing chamber which facilitates dispensing of buffered local anesthetic solution instantly prior to administering the solution into the intended target tissue;
- it provides a syringe system for simultaneously transferring solutions in preset ratios and amounts from a dual-reservoir carpule directly into a mixing chamber;
- it provides a syringe with an autoclavable (sterilizable) mixing chamber; it provides a syringe with a reusable mixing chamber;
- it provides a syringe mixing chamber causing turbulence between the two solutions when the slotted plunger is actuated;
- it provides a syringe assembly with piercing needles for providing fluid transfer paths or conduits from each reservoir of the partitioned carpule into a common mixing chamber; and
- it provides a partitioned carpule assembly having the same length and where the diameter of a standard carpule but having one reservoir smaller than the other (8:1 ratio).

In use, a syringe of the subject invention is manipulated and utilized in a manner similar to a conventional carpuleholding syringe, except that the carpule is partitioned to have dual reservoirs, each loaded within the syringe barrel prior to administration of a medicament.

Specifically, the method comprises the steps of:

a) providing a syringe having a syringe barrel capable of receiving a single partitioned carpule, a slotted plunger, and mixing chamber, as described herein;

b) loading the carpule containing a drug solution and buffer solution into the syringe barrel; and c) actuating, in a single step, the slotted plunger to actuate each reservoir to expel and deliver anesthetic solution and buffering solution into a mixing chamber, whereby the anesthetic solution and buffering solution are mixed, preferably homogeneously, and delivered from the delivery port as a buffered anesthetic solution and through a hypodermic transfer needle into a target tissue.

The method can further include removing the expended carpules from the syringe barrel and repeating the above steps a) through c) as needed.

It is contemplated that the invention provides a significant role in ease-of-use and efficiency in administering local anesthetic buffered solution in a pH control fashion. The present invention provides optimal dosing control of freshly buffered local anesthetic solution at the fingertips of medical practitioners.

It is to be understood that certain descriptions of the invention have been simplified to focus on elements that are relevant for a clear understanding of the invention, while eliminating, for purposes of clarity, other elements that those of ordinary skill in the art will appreciate may also comprise a portion of the invention. While the present invention has been presented in accordance with several preferred and practical embodiments thereof, it is recognized that departures from and variants of the instant disclosure are contemplated as being fully within the spirit and scope of the invention.

The invention claimed is:

1. A mixing cartridge syringe comprising:

i) a cartridge syringe comprising a single barrel for receiving a single carpule, said single carpule defining a carpule chamber. the carpule chamber being partitioned longitudinally and asymmetrically within the chamber, along a long axis of the single carpule to form a first reservoir for containing a drug solution and a second reservoir for containing a buffering solution, wherein the first reservoir is distally capped with a first sliding cap and the second reservoir is distally capped with a second sliding cap;

ii) a single plunger comprising a plunger stem comprising a slot formed longitudinally and off-center forming two asymmetric and integrally connected plunger stem portions of equal length which separately and matingly engage each of the first reservoir sliding cap and the second reservoir sliding cap provided on a distal end of each of the first and second reservoirs for expelling the contents therefrom; and iii) a mixing chamber for receiving and mixing the drug solution and the buffering solution expelled from the single partitioned carpule, the mixing chamber containing a turbulence apparatus disposed therewithin, said turbulence apparatus being operable to facilitate mixing of the drug solution and the buffering solution within the mixing chamber before administering the drug solution and buffer solution to a patient.

2. The mixing cartridge syringe of claim 1, wherein the mixing chamber is in fluid communication with the first reservoir through a first conduit comprising a first piercing needle operable to traverse an end cap on the proximal end of the first reservoir and is in fluid communication with the second reservoir through a second conduit comprising a second piercing needle operable to traverse an end cap on the proximal end of the second reservoir.

3. The mixing cartridge syringe of claim 1, wherein each plunger stem portion of the slotted plunger stem comprises a harpoon on its proximal end.

4. The mixing cartridge syringe of claim 1, wherein the turbulence apparatus is distinct and separate from the mixing chamber.

5. The mixing cartridge syringe of claim 1, further comprising an exit port connectable with a hypodermic transfer needle.

6. The mixing cartridge syringe of claim 1, wherein the turbulence apparatus is formed from an inert material.

7. The mixing cartridge syringe of claim 6 wherein the inert material is steel wool.

8. The mixing cartridge syringe of claim 6 wherein the inert material is polymeric.

9. The mixing cartridge syringe of claim 6 wherein the inert material is plastic.

* * * * *